(12) United States Patent
Husmann et al.

(10) Patent No.: US 9,063,009 B2
(45) Date of Patent: Jun. 23, 2015

(54) NONDESTRUCTIVE TESTING OF A CARRIER ELEMENT OF AN ELEVATOR INSTALLATION

(75) Inventors: Josef Husmann, Lucerne (CH); Guntram Begle, Weggis (CH)

(73) Assignee: Inventio AG, Hergiswil (CH)

( * ) Notice: Subject to any disclaimer, the term of this patent is extended or adjusted under 35 U.S.C. 154(b) by 228 days.

(21) Appl. No.: 13/811,504

(22) PCT Filed: Jul. 7, 2011

(86) PCT No.: PCT/EP2011/061509
§ 371 (c)(1),
(2), (4) Date: Jan. 22, 2013

(87) PCT Pub. No.: WO2012/010431
PCT Pub. Date: Jan. 26, 2012

(65) Prior Publication Data
US 2013/0119256 A1     May 16, 2013

(30) Foreign Application Priority Data

Jul. 23, 2010 (EP) .................................... 10170686

(51) Int. Cl.
*G01J 5/10* (2006.01)
*G01N 27/82* (2006.01)
*B66B 7/12* (2006.01)

(52) U.S. Cl.
CPC . *G01J 5/10* (2013.01); *G01N 27/82* (2013.01); *B66B 7/1238* (2013.01)

(58) Field of Classification Search
CPC ........................................................ G01J 5/10
USPC ................................. 250/341.8, 338.1, 341.1
See application file for complete search history.

(56) References Cited

U.S. PATENT DOCUMENTS

| 5,198,765 A | 3/1993 | Van Der Walt |
| 5,804,964 A | 9/1998 | Hamelin et al. |
| 7,012,398 B2 * | 3/2006 | Ebihara et al. ................ 318/649 |

FOREIGN PATENT DOCUMENTS

EP        0271728 A2    6/1988

* cited by examiner

*Primary Examiner* — David Porta
*Assistant Examiner* — Faye Boosalis
(74) *Attorney, Agent, or Firm* — Fraser Clemens Martin & Miller LLC; William J. Clemens

(57) ABSTRACT

A testing device includes a receiving unit for electromagnetic signals arranged on a carrier element to be tested to generate test data from received electromagnetic radiation. The test data are evaluated in a processing system to determine a deviation of the test data from a nominal state of the carrier element. The testing device is used to test a carrier element of an elevator installation on which the elevator car is suspended.

15 Claims, 5 Drawing Sheets

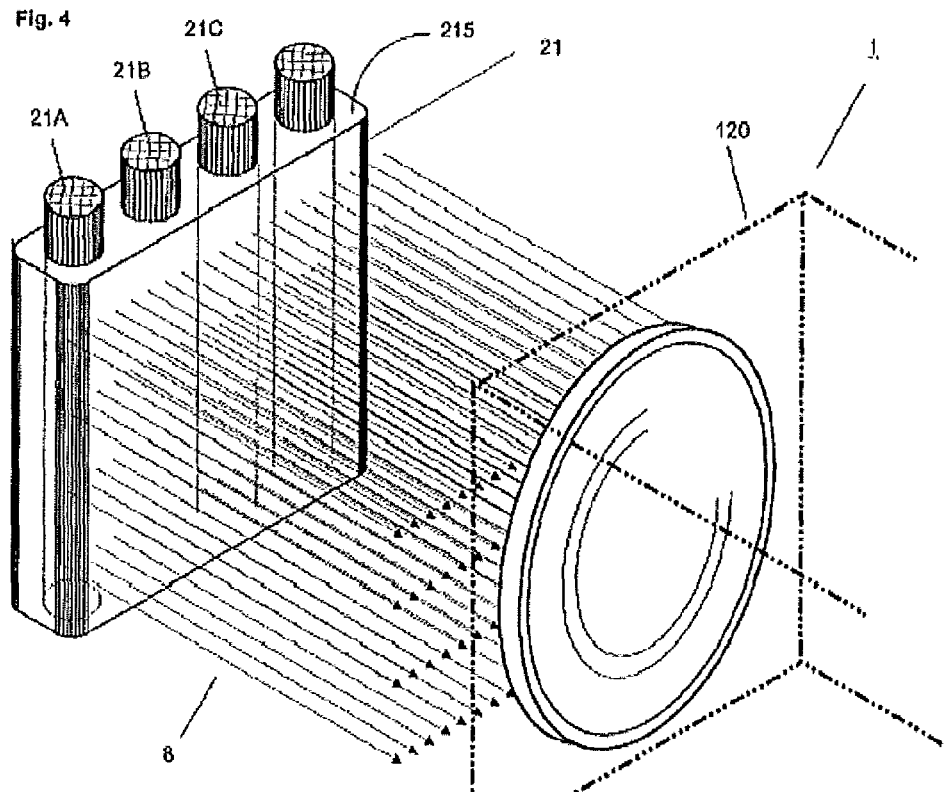
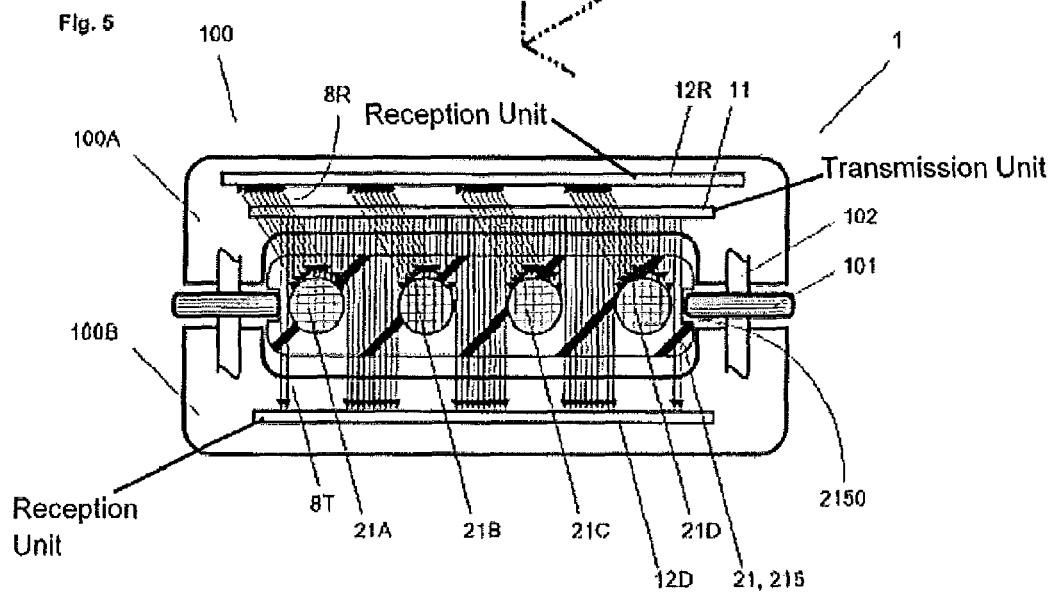

NONDESTRUCTIVE TESTING OF A CARRIER ELEMENT OF AN ELEVATOR INSTALLATION

FIELD

The invention relates to a method and a device for nondestructive testing of a carrier element in an elevator installation.

BACKGROUND

An elevator installation is installed in a building and substantially consists of a car which is carried by one or more carrier elements. In a known elevator installation a drive acts on the carrier elements in order to displace the car along substantially vertical guide rails. The elevator installation is used to convey people and goods over individual or a number of floors within the building.

The carrier elements can be embodied as individual round ropes made of metal (steel). By way of example, each round rope has a diameter of approximately 8-10 mm and is stranded from individual strands, which in turn consist of individual wires. The round ropes are usually not sheathed, and so the stranding is visible on the surface thereof. Depending on the application, it is also possible for these carrier elements to be sheathed; then the individual strands or wires are not visible.

However, the carrier elements can also be flat ropes or flat belts, which have a rectangular cross section; i.e., such flat belts are wider than high (thick). A flat belt consists of individual thin steel ropes or tension members, which are embedded in a plastic and are sheathed by the latter. The steel ropes, or tension members, take up tensile forces while the plastic, inter alia, protects the steel ropes from external environmental effects and, for example, ensures a desired traction on a drive pulley of the elevator installation.

The carrier elements can also consist of tension members in the form of non-metallic ropes and strands. Such non-metallic strands, or tension members, can for example be made of carbon or silicon fibers, of aramid or glass fibers, etc. These non-metallic ropes or strands are generally embedded in a plastic sheath. The ropes or strands take up tensile forces while the plastic sheath, inter alia, protects the ropes or strands from external environmental effects and, once again, ensures a desired traction on a drive pulley of the elevator installation. These non-metallic carrier elements can likewise be embodied with a round design in the form of flat ropes or as flat belts.

In order to ensure the safety of elevator installations, the utilized carrier elements are tested at regular intervals. In the process, a test is undertaken to see whether defects, such as kinks, loop formation, breaks of strands and wires, loosenings of the outer layer, or pinches have occurred. Use can be made of various technologies and methods for testing. By way of example, known methods are based on a visual inspection by a servicing engineer or a measurement of electrical (e.g. resistance) or magnetic (e.g. magnetic flux) properties.

In order to test the carrier elements having metallic ropes or strands, use can for example be made of methods in which the carrier element is exposed to magnetic fields and changes in the magnetic flux are determined. U.S. Pat. No. 5,198,765 has disclosed a method in which a magnetic field is generated by means of a magnetizing head, with a carrier element being moved through said field in the axial direction. In the process, the carrier element is magnetically saturated at a first location. Provision is made at a further location for a scanning apparatus, by means of which magnetic flux changes in the carrier element are determined, with said magnetic flux changes being related to a cross-sectional change in the carrier element. U.S. Pat. No. 5,804,964 describes that leakage flux can also occur if individual wires are interrupted and that this leakage flux emerges from the carrier element and is detected by means of a Hall sensor.

In order to test carrier elements with non-metallic carrier elements, solutions with so-called indicator strands are known, with the latter being inserted into the carrier element. Wear and tear of the carrier elements can be identified by means of these indicator strands.

The inspection of the carrier element becomes more difficult if it has a sheath. Damages which are already so serious that they are already visible from the outside can be identified despite the sheath. However, the sheath prevents emerging damage, which is initially still small, from being visible from the outside. This externally non-visible damage to the tension member constitutes a potential risk to safety. A purely visual inspection by a servicing engineer therefore does not suffice.

SUMMARY

The present invention is therefore based on the object of specifying a technology for reliable and nondestructive testing of a carrier element, more particularly a carrier element provided with a sheath, in an elevator installation. Testing the carrier element should provide reliable data which render it possible to establish relevant information in respect of the actual state of the carrier element such that the replacement state of wear thereof can be determined. Here, measurement results should where possible not be influenced by sheaths, deposits and dirtying, such as lubricant, plastic sheaths, oil splatters, wear debris particles etc., which may surround the carrier element under certain circumstances or be deposited thereon.

In order to achieve this object, the technology described here uses a reception unit for electromagnetic radiation which is directed at a carrier element to be tested in order to generate test data from received electromagnetic radiation with a wavelength in the range of between 30 μm and 950 μm, preferably in the range of between 90 μm and 120 μm. The test data is evaluated in a processing apparatus in order to determine a deviation of the test data from an intended state of the carrier element. This technology preferably serves for nondestructive testing of at least one carrier element in an elevator installation, in which the carrier element carries a car.

According to one embodiment, recordings (or a series of recordings) are made of the carrier element and these recordings are compared to ideal state patterns, i.e. to state patterns which represent a good or acceptable state of the carrier element. This evaluation of the recordings is preferably performed by means of automated computer-assisted evaluation algorithms, for example by means of software for evaluating recordings. Thus, transitions between materials of differing density, differing electrical conductivity or differing transparency on the carrier element can be captured, for example by edge extraction in the recordings. It is expected that these edge transitions should result in a line pattern determined in accordance with the longitudinal alignment of the carrier element. Irregularities, such as interruptions, indentations or bulges, in this line pattern indicate wear and tear or a defect of the carrier element and, if such irregularities occur frequently, the carrier element needs to be replaced or inspected more selectively.

According to another exemplary embodiment, reference images of a carrier element are created after the carrier element is installed and these images are stored in a database. These reference images represent the intended state of a carrier element. In these reference images, it is mainly the surface of the carrier element or, depending on the type of test radiation or depending on the transparency state of the sheath, also surfaces of ropes, strands and wires which are embedded in a sheath that is/are visible. During the use of the carrier element, these surfaces of the carrier element and the embedded elements change, particularly after relatively long use. By way of example, if wires break or buckle, groups of wires or individual strands project from the carrier element or from a laid rope present in the carrier element. These projecting strands can penetrate a sheath and be visible from the outside. If an image recording (or a series of image recordings) is then made of the same location and compared to the stored image, the broken strands or buckling can be identified. These image recordings are preferably also evaluated by means of automated computer-assisted evaluation algorithms, for example by means of software for evaluating images.

The exemplary embodiments of the technology, described here, firstly enable the testing of carrier elements which merely consist of metallic laid wire ropes or which have a sheath in which at least one (laid) wire rope or one strand is integrated or embedded. Here, the integrated wire ropes and strands can be tested without the sheath being opened or removed. In one embodiment of the technology, it is furthermore possible to test the state of the sheath. In a further embodiment of the technology, it is also possible, on the other hand, to test carrier elements with non-metallic rope and strand structures.

In one exemplary embodiment, provision is made for at least one transmission unit and at least one reception unit, which are respectively suitable for emitting and for receiving electromagnetic radiation. The wavelength of this electromagnetic radiation lies in the range of between approximately 30 μm and approximately 950 μm. In a further exemplary embodiment, use is made of radiation in the visible range of between approximately 400 nm and approximately 800 nm in addition to the electromagnetic radiation in the range of between approximately 30 μm and approximately 950 μm. The received electromagnetic radiation is used to form transmission patterns and/or reflection patterns in an evaluation unit, which patterns are evaluated in order to establish surface or contour changes on the carrier element, or of the ropes and strands embedded in the carrier element.

In order to capture test radiation which lies in the range of visible light, daylight or artificial light is used in a simple embodiment, said light being emitted by a shaft illumination. Light radiation reflected at the surface of the carrier element can therefore be captured by means of photosensors which are present in the reception unit. Furthermore, the visible shadow cast by the carrier element can be recorded. The reception unit, for example a camera (preferably a digital camera, or a digital video camera, which generates digital image recordings from light reflected by the surface of the carrier element), and the transmission unit or the light source (should daylight be insufficient) can therefore be arranged on the same side or, preferably, on mutually diametrically opposed sides of the carrier element. It is generally sufficient to identify relatively large damage. Hence low resolutions, for example a resolution of less than 1 megapixel, are already completely sufficient. This test radiation is preferably used if the visible surface of the carrier element needs to be monitored.

Non-visible test radiation, the wavelength of which lies in the range of between 30 μm and 950 μm, preferably in the range of between 90 μm and 120 μm, is emitted along a transmission axis by an appropriately designed transmission unit and is acquired by a reception unit which is provided on the opposite side of the carrier element or by a reception unit which is aligned along one or more reflection axes and originates in the carrier element. In this case, the reception unit is designed to receive electromagnetic radiation in this wavelength range. This test radiation is preferably used for testing carrier elements with a non-transparent sheath, such as rubber or colored polyurethane. Electromagnetic radiation in this range penetrates such sheaths. Accordingly, these sheaths are transparent to this test radiation. It is naturally also possible to use this electromagnetic radiation to test carrier elements with a transparent sheath.

In one embodiment the reception unit comprises a plurality of reception sensors which are arranged along different axes. This renders it possible to generate a 3-dimensional image of the surface.

In general, it is by all means sufficient if accumulations of breaks of wires or fiber regions can be identified. Such accumulations create damages of more than 1/10 mm in the contours. The aforementioned test radiation, the wavelength of which lies in the region of approximately 100 μm, is suitable for identifying such errors. In order to identify such damages, significantly reduced resolutions of the capturing units are also sufficient. By way of example, thermal imaging cameras can be used for this, the resolution of which for example lies in the region of 480×320 pixels, or, in a particularly expedient embodiment, use can also be made merely of individual or a few sensor rows, for example corresponding to a resolution of 3×320 pixels. The reception unit is then moved continuously, like in a photocopier, along the carrier element, as a result of which a complete image of the carrier element is created. Naturally, it is irrelevant here whether the carrier element is moved past the reception unit or whether the reception unit is guided along the carrier element.

In a development of this test methodology, it is feasible to heat the carrier elements a little, for example by means of an induction coil. In the process, only metallic tension members, or strands or ropes, are heated by the induction. The heated tension members generate radiation corresponding to this temperature. A thermal imaging camera can be used to capture the thermal profile of the tension member. This thermal imaging camera is provided with a lens which renders it possible to capture test radiation with a wavelength then lying in the range below 30 μm, typically in the region of approximately 10 μm. In the case of faults in the metallic cross section of the tension members there are also deviations in the thermal profile of the tension member. This thermal profile can in turn be evaluated by means of one of the methods described above, by means of image comparison or by means of an edge extraction method.

Practically all changes that occur e.g. in a rope or strand can have a significant influence on the surface condition of the rope or of the strand. The peripheral strands, wires or fibers of a rope are normally exposed to increased load because they are in contact with guide and deflection elements of the elevator installation and therefore greatly exposed to mechanical stresses. Furthermore, stronger tension or bending forces usually occur in peripheral strands, wires or fibers rope, which forces can lead to a complete or partial break of strands, wires or fiber strands. Furthermore, environmental influences, aging influences or other external effects mainly cause changes on the outer surface of a metallic object. Corrosion therefore occurs firstly and predominantly on the surface of wire ropes. However, environmental or aging influences and other external effects also influence non-metallic materials or also influence the plastic sheath of the carrier elements.

Defects therefore occur nearly exclusively in the peripheral region of the rope, which is why testing the surface condition can already for this reason provide essential information in respect of the condition of the carrier element.

By contrast, to the extent that optically unidentifiable interruptions occur within the rope, the peripheral strands, wires or fiber strands experience stretching under the acting load, likewise leading to a change in the surface condition and the dimension (diameter) of the rope. By capturing and analyzing the dimensions, and/or the surfaces of the carrier element, or of the embedded ropes, strands or wires, it is possible to assess the state thereof. As already explained above, it is generally only necessary to identify summations of errors, which then bring about damage of a number of 1/10 mm. Such defects can be captured sufficiently accurately by means of radiation in the aforementioned wavelength range of 90 μm to 120 μm.

The described embodiments of the technology therefore permit the establishment of status information which suffices for determining the replacement state of wear of the carrier elements. There moreover is the option of combining the present technology with more complicated further testing methods, or the evaluation by means of test radiation in the visible and non-visible range can be combined. To the extent that a change of the contour or surface structure of a rope was determined, it is also possible, for example, to X-ray the rope using X-ray methods. If this more complicated method, which harbors safety risks, is required, it can therefore be reduced to a single region of the carrier element. Thus there is greatly reduced complexity, even in the case of combination with further methods.

The apparatus which contains the reception units and an associated evaluation unit is preferably equipped with a marking apparatus. The marking apparatus marks the relevant point of the carrier element, for example by means of a colored dot, if a defect is detected. As a result, this point can be found easily for a more detailed analysis.

Preferably electromagnetic test radiation with a wavelength in the range of between 30 μm and 950 μm, i.e. in the long-wave region of infrared radiation, is used in a first exemplary embodiment. Here, the wavelength is selected such that, firstly, it passes through dielectric materials and that, secondly, electrically conductive materials, such as e.g. metallic materials, reflect the test radiation. In order to penetrate the sheath of a carrier element, which for example consists of rubber or polyurethane (PU), use is preferably made of test radiation with a wavelength in the range of between 90 μm and 120 μm. For test radiation with wavelengths in this range, the sheath of the carrier elements, and possible deposits such as oils and fats, are transparent or they have a relatively low transmission resistance. Accordingly, this embodiment is particularly recommendable in the case of dirtied carrier elements.

As a result of scanning the carrier elements by means of the test radiation it is therefore possible to form transmission patterns which correspond to the "shadow cast" by the metallic portion of the carrier element. If the shadow cast deviates from a substantially regular straight-lined profile, this is typically caused by peripheral defects of the carrier element such as compressed or broken wires or other faults in the carrier element. In one exemplary embodiment, these defects can be captured and evaluated by evaluating the transmission pattern. To the extent that the faults in the rope or the strands have an influence on the surface of the carrier element itself, for example by broken or compressed wires emerging from the sheath, these defects can, according to another exemplary embodiment, naturally also be captured in complementary fashion by means of an image generation in the visible wavelength range on the basis of the reception unit provided for this.

As a result of scanning the carrier elements by means of the test radiation, these are reflected by the metallic portion of the carrier element. This reflected test radiation extends along a reflection axis to a further reception unit, which is able to capture this reflected radiation and images the latter as reflection pattern. This reflection pattern contains valuable information in respect of the state of the metallic portion of the carrier element and thus enables the analysis of the carrier element or of the metallic portion of the carrier element. In the process, it is possible to identify further faults in the carrier element, particularly damage to the surface structure. Naturally, it is also possible here to apply further detailed analyses, as described above.

Provided that defects occur within the cross section of the carrier element, these can be detected by inspecting resulting changes on the surface, such as compressions or constrictions.

The test can be carried out in a particularly exemplary fashion by virtue of using reference patterns. Advantageously, reference patterns can be used which were recorded of the test item itself, for example recorded prior to use thereof, and constitute an intended state. Particularly precise measurement results can be achieved if stored transmission patterns and reflection patterns (for example recorded by a video camera) are precisely assigned to the individual sections of the carrier element and compared to currently recorded transmission patterns and reflection patterns of the same sections. Reference patterns corresponding to the sections are then used to establish irregularities.

To this end, use is for example preferably made of carrier elements which are marked over the whole length. These markings can be stamped into the sheath. The carrier elements can furthermore be marked by means of colors. RFID chips are integrated into the sheath in other embodiments. The markings can be read by means of readers, optical scanning devices or RFID readers, and the individual sections of the carrier element can be identified and the appropriate reference patterns can be loaded. Furthermore, it is possible to identify a section of the carrier element by calculation on the basis of the position of the elevator car.

Naturally, the test can also be carried out by merely evaluating the contours or edges of the transmission and reflection patterns. In the case of an intact carrier element, all contours on and in the carrier element form substantially straight lines which extend in parallel. Indentations or bulges or frays of these contours indicate a fault in the carrier element and can be analyzed in detail. This embodiment requires little storage space because, in particular, there is no need to store reference data.

Such a test is advantageous if existing carrier elements, which in part have already been in operation for years, have to be evaluated. There are no specific reference data for these carrier elements.

All these method variants, firstly recording and evaluating transmission patterns and secondly recording and evaluating reflection patterns, and the associated evaluations by means of reference data or evaluation of the contours and edges, can be applied individually and they enable an appropriate test of the carrier element. As a result of an optional combination of these method and evaluation options, it is possible, where necessary, to obtain a significantly higher reliability. Here questions which occur in one method variant can be answered on the basis of test results which are established by the other method variant. Furthermore, it is possible to increase the reliability of the test by virtue of carrying out measurements in various wavelength regions.

Thus, provision is made in one exemplary embodiment for the capture of reflection patterns and transmission patterns to take place in a plurality of test steps by means of electromagnetic test radiation with different wavelengths. As a result of using test radiation with wavelengths in the range of between 30 µm and 950 µm, preferably in the range of 90 µm-120 µm, it is possible to establish the shadow cast and the surface condition of the metallic portion of the carrier element. As a result of using test radiation with wavelengths in the visible range, it is possible to establish and test the shadow cast and the surface condition of the sheath itself. At the same time, it is possible to detect optionally provided markings on the carrier element.

Reflections are preferably captured along a reflection axis, which, together with the transmission axis, includes an angle, which—with an arc extending from the transmission unit to the reception unit—includes an angle lying in the range of between 0° and 90° or in the range of between 0° and −90°, or between +/−π/2. Radiation captured in this angular range permits the imaging of substantial portions of the carrier element. In one embodiment variant, two reception sensors are associated with a transmission unit, said reception sensors being arranged in different angular ranges. This renders it possible to capture a substantially three-dimensional element. Two receptions units are preferably respectively arranged at an angle of +/−45° with respect to the reception unit, i.e. offset by 90° from one another.

Alternatively, or in combination, the transmission unit and the at least one reception unit are held by a rotatable carrier device and rotated, or swiveled, between at least two positions about the carrier element in order to scan the carrier element from at least two sides. As a result of using the rotatable or swivelable carrier device, it is possible to carry out a complete test of the carrier element using few reception sensors. The carrier device is preferably controlled by means of a calculation unit, which likewise serves to evaluate the test radiation. The evaluation unit is preferably connected to a data storage medium or a database, from which stored data relating to the utilized carrier elements can be recalled.

The transmission unit for generating wavelengths in the non-visible range preferably uses lasers, for example two-color diode lasers, which generate two different light frequencies. A beat is created by superposing these two light frequencies. A photoconducting antenna acts as low-pass filter and emits the resultant radiation. The use of a quantum cascade laser is also possible. This transmission unit can be used to set wavelengths in the range of between approximately 30 µm and 500 µm.

The transmission unit and the reception unit aligned along the reflection axis are preferably integrated into a module such that a simple and cost-effective design of the test device can be realized. As a result of this, it is possible to use two or more of the integrated modules, which are for example held by controllable mechanical arms. Here, the reception unit of one module can receive reflected test radiation from the same module and test radiation, transmitted from another module, along the transmission axis.

In one embodiment, the transmission unit and the reception unit are coupled directly to the carrier element and kept at a defined distance therefrom. This is how it is possible always to capture transmission patterns and reflection patterns in the same fashion and with an optimized quality. The transmission unit and the reception unit are preferably arranged in a housing that can be displaced along the carrier element, or along which the carrier element is guided. In the first case, the housing with transmission unit and reception unit is, for example, arranged on an elevator car and is displaced along the carrier element therewith and, in the second case, the housing is, for example, affixed in the shaft and the carrier element is guided along the housing. Naturally, the housing with integrated transmission and reception unit also has appropriate guide means, such as rollers, wheels or sliding elements, which enable exact positioning of the carrier element in relation to the housing.

DESCRIPTION OF THE DRAWINGS

In the following text, the invention will, in conjunction with the figures below, be explained in more detail on the basis of a plurality of exemplary embodiments. In detail:

FIG. 4 shows a schematic illustration of a further exemplary embodiment of a test device, by means of which a flat carrier element is tested in a second arrangement;

FIG. 5 shows a schematic illustration of a further exemplary embodiment of a test device which is directly coupled to a flat carrier element as per FIG. 3 or FIG. 4;

DETAILED DESCRIPTION

Figure 1:
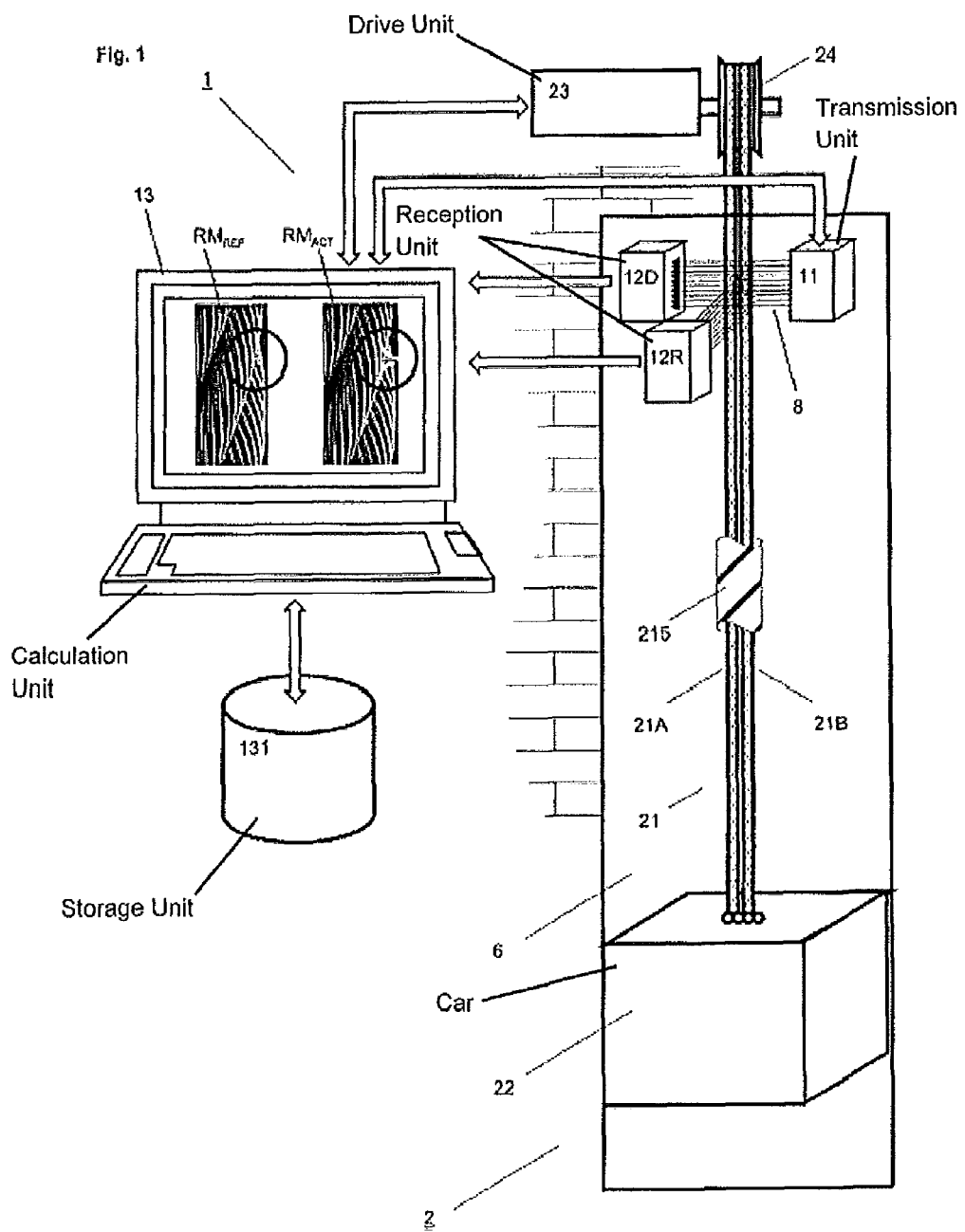
FIG. 1 shows a schematic illustration of an exemplary embodiment of an elevator installation with carrier elements which are tested by means of a test device.

FIG. 1 shows a schematic illustration of an exemplary embodiment of an elevator installation 2, which has an elevator car 22 which can be displaced vertically in an elevator shaft 6 and is connected to a drive unit 23 via carrier elements 21 and a drive pulley 24. Further components of the elevator installation 2 (e.g. counterweight and safety apparatuses) or details in respect of the suspension of the elevator car 22 (e.g. 1:1, 2:1, etc. suspension) are not shown in FIG. 1 for reasons of clarity. However, it is understood that the exemplary embodiments described here can be used independently of these components or details, mentioned in an exemplary fashion, in the elevator installation 2.

The elevator installation 2 is furthermore provided with a test device 1 by means of which a carrier element 21 can be tested. In the illustrated exemplary embodiment, the carrier element 21 comprises a sheath 215 made of plastic in which, for example, two wire ropes 21A, 21B are integrated. However, it is understood that more than two wire ropes can be embedded in the sheath 215 in a different exemplary embodiment. The plastic in this exemplary embodiment is not transparent to visible light, and so the wire ropes 21A, 21B cannot be seen from the outside. Depending on the embodiment of the carrier element 21—round rope or flat rope/belt—the sheath 215 has a curved surface, as indicated in FIG. 1 for a round rope, or at least one flat surface for a flat rope. As mentioned above, a flat rope is wider than high/thick.

It is understood that the test device 1 is not restricted to testing sheathed carrier elements 21. In principle, the test device 1 is also suitable for testing carrier elements 21 which have no, only a thin or a transparent sheath. By way of example, it may be the case that the surface of part of a non-sheathed carrier element 21 has deposits, wear debris or dirtying such that the actual surface of the carrier element 21 is not visible. The test device 1 preferably renders it possible to test such a surface part as well.

In one exemplary embodiment, the test device 1 has one transmission unit 11 and two reception units 12D, 12R, which are connected to a calculation unit 13. The calculation unit 13 serves to control the test device 1 and to evaluate the data received from the reception units 12D, 12R. A result or part of a result of the evaluation can be displayed on a monitor or screen in the illustrated example, for example as intended and actual states. The calculation unit 13 can be a mobile unit, which is or can be connected to a central elevator control, for example via an interface unit, when required or during service works. As an alternative thereto, the calculation unit 13 can be part of the elevator installation 2 which permanently remains in the elevator installation 2. In one embodiment variant, the calculation unit 13 works together with the elevator control. Thus, for example, the elevator control for example actuates the drive unit 23 in accordance with the evaluation progress of the calculation unit 13 in order to move the carrier elements 21 past the transmission unit 11 and the reception units 12D, 12R. The calculation unit 13 accordingly activates the transmission unit 11 and the reception units 12D, 12R. Naturally, all safety functions of the elevator control are also activated during such a test operation, although the movement is generally at a reduced travel velocity in this case.

In general, the test device is only used temporarily for the purpose of testing the carrier elements in the elevator installation. To this end, the elevator installation is closed for passenger transportation and the test device is attached together with the evaluation units, preferably in the vicinity of the elevator drive, such that a carrier element can be tested. The car is subsequently displaced at a low, uniform velocity of approximately 0.1 m/s over the whole operating range. In the process, the test device measures faults in the carrier element and outputs these by means of a test log, signal tone or by marking this, etc. In this fashion, the servicing staff measures all carrier elements installed in the elevator installation. As a final step, the servicing specialist inspects the points of the carrier elements marked as critical and makes a decision in respect of possibly replacing the carrier element.

Figure 3:
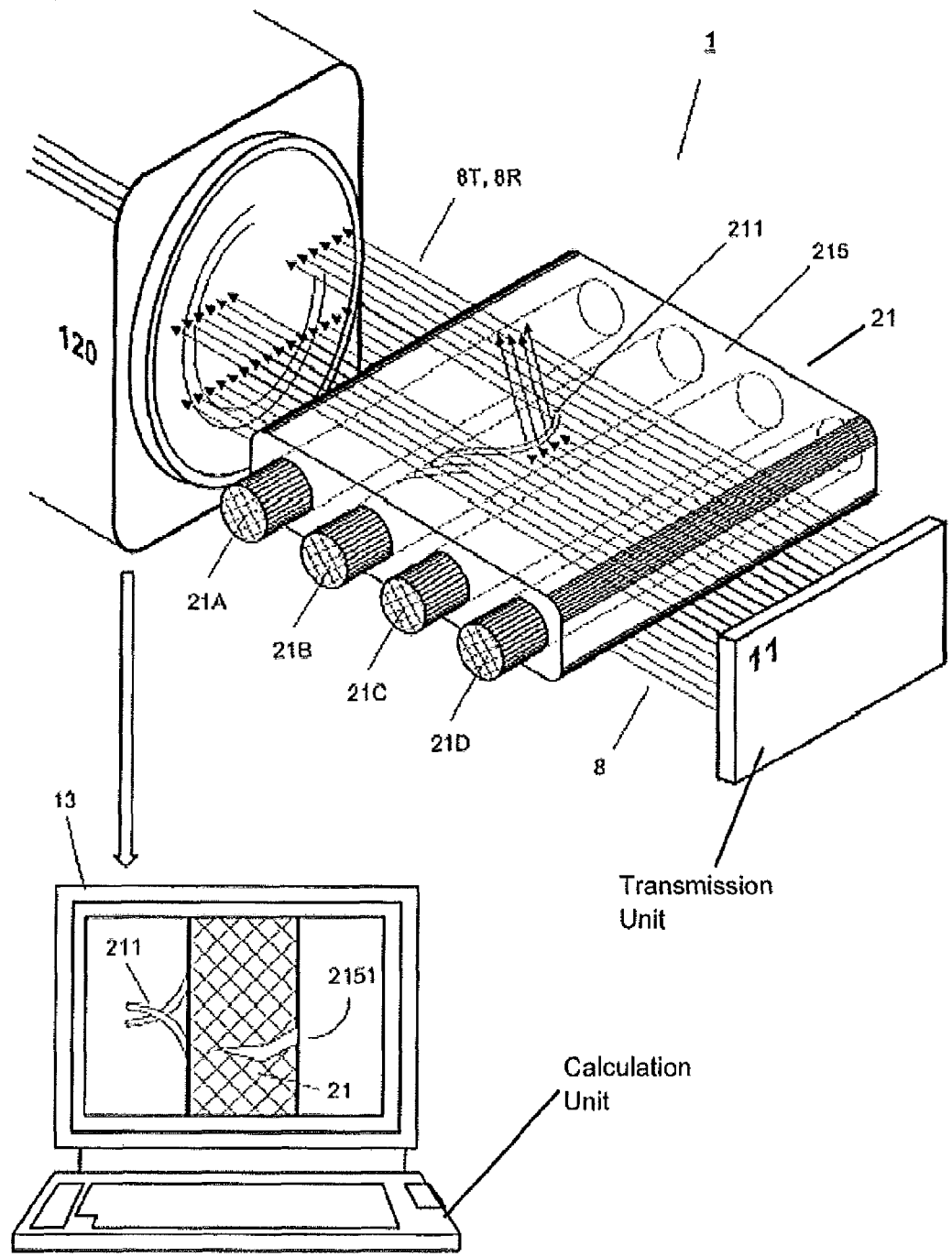
FIG. 3 shows a schematic illustration of a further exemplary embodiment of a test device, by means of which a flat carrier element is tested in a first arrangement.

Deviating from the exemplary embodiment shown in FIG. 1, the test device 1 can have only one reception unit 12D, 12R. As shown in FIG. 1, this reception unit can be arranged in the shaft 6. FIG. 3 (see below) illustrates an exemplary arrangement. If enough daylight or another light source is present in the shaft 6, it is likewise possible to dispense with the transmission unit 11. An exemplary embodiment of this arrangement is shown in FIG. 4 (see below).

As illustrated, the calculation unit 13 is connected to a storage unit or a database 131, in which reference data (reference patterns) are stored. In one exemplary embodiment (not illustrated), the database 131 is present in the calculation unit 13 or integrated into the latter. The reference data describe "ideal", i.e. undamaged, carrier elements 21 in an intended state. The test device 1 then uses these reference data to carry out an intended state/actual state comparison, as described in more detail below, the result of which the calculation unit 13 can illustrated pictorially.

In one exemplary embodiment, the calculation unit 13 is a computer unit in which, inter alia, a processor and an evaluation program are installed. The evaluation program executes a fixed evaluation algorithm, as described in an exemplary fashion below. The computer unit communicates with the transmission unit 11, the reception units 12D, 12R and the drive 23. The computer unit processes received radiation as per the installed evaluation program and outputs processing results or parts thereof on the monitor or screen.

The carrier elements 21 can be tested during the normal operation of the elevator installation 2 or else during a test operation of the elevator installation 2. When the user is not using the elevator installation 2 (for example at night or over the weekend), the latter could for example independently change into a test mode, in which specific sections of the carrier elements 21 are tested. Here, in one exemplary embodiment, the calculation unit 13 can register which sections have already been tested.

A reception unit, as used in the exemplary embodiments described here, has a sensor unit (e.g. a multiplicity of sensors (e.g. CCD sensors for the substantially visible radiation range and micro-bolometers for the non-visible range) which can be arranged in a sensor array) which is sensitive to the wavelength range of the utilized electromagnetic radiation. Such sensors are known, for example, from use in a digital camera or in thermal detectors.

Figure 2:
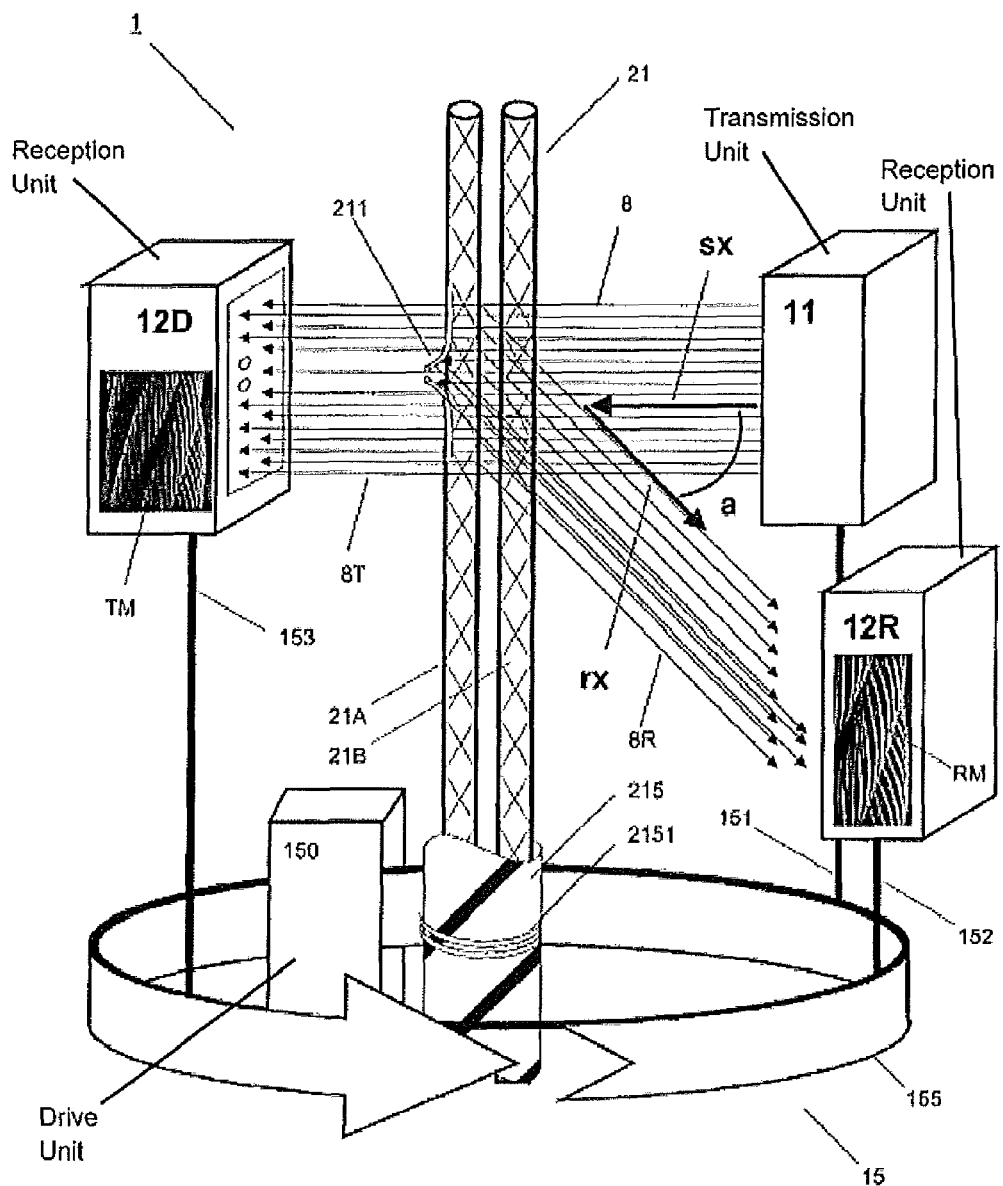
FIG. 2 shows a schematic illustration of an exemplary embodiment of the test device from FIG. 1.

FIG. 2 schematically shows an exemplary embodiment of a test device, in which electromagnetic test radiation 8 emitted by the transmission unit 11 is fed to the first reception unit 12D via the transmission axis sx and to the second reception unit 12R via a reflection axis rx, which has its origin on the carrier element 21. Using test radiation 8T received along the transmission axis sx (downstream of the carrier element 21 as viewed from the transmission unit 11) transmission patterns TM are formed in the calculation unit 13, of which transmission patterns one is shown symbolically in FIG. 2. Reflection patterns RM are formed in the calculation unit 13 on the basis of the test radiation 8R received along the reflection axis rx, of which reflection patterns one is likewise shown symbolically in FIG. 2.

The transmission pattern TM shows the silhouette of or the shadow cast by the carrier element 21. Depending on the wavelength of the electromagnetic test radiation, the silhouette of the sheath 215 (in the case of wavelengths in the nm range) or the silhouette of the metallic wire ropes 21A, 21B (in the case of wavelengths in the pm range) is measured. The reflection pattern RM, formed on the basis of reflected electromagnetic test radiation, shows the structure of the surface of the metallic wire ropes 21A, 21B in a detailed illustration and typically has a greater information content than the transmission pattern TM.

FIG. 2 shows that a peripherally arranged wire 211 of one of the wire ropes 21A has broken open and the wire ends thereof protrude outward or are frayed out. As a result of this damage, there is an influence on both the transmission pattern TM and the reflection pattern RM, as indicated in FIG. 2. The laterally protruding wire ends 211 interrupt the test radiation at the relevant point and reflect a corresponding radiation portion back via the reflection axis rx. Thus radiation portions are missing in the relevant region for the formation of the transmission pattern TM while there are additional radiation portions in the relevant region for forming the reflection pattern RM. Increased reliability can therefore be achieved by simultaneously forming and monitoring the transmission pattern TM and the reflection pattern RM. In the process, it is sensible to compare the results of the two test channels to one another. As a result, it is possible not only to make the measurement results more precise but the correct function of both channels is also tested at the same time.

It is possible to determine changes by comparing the transmission patterns TM and reflection patterns RM, recorded by the reception units 12D, 12R, with respectively one reference pattern RM of the intended state. In FIG. 1, a reference pattern $RM_{REF}$ and a currently recorded reflection pattern $RM_{ACT}$, which are compared to one another, are shown on the screen of the calculation unit 13. The reflection pattern RM consists of a strip pattern in e.g. different levels of gray and corresponds to a "fingerprint" of the carrier element 21 and can be processed accordingly in order to determine relevant differences. By way of example, a method for comparing fingerprints is known from U.S. Pat. No. 7,333,641. This method serves to analyze striped image patterns, as also occur when recording reflection patterns. In the reflection patterns recorded according to the invention, strips are caused by the individual strands of the carrier element 21A or 21B.

Methods for automatic face recognition are also based on a comparison between a stored image (reference face) and a currently recorded image (actual image). The article "Video-based framework for face recognition in video" by Dmitry O. Gorodnichy, Proceedings of Second Canadian Conference on Computer and Robot Vision, pages 330-338, British Columbia, Canada, May 9-11, 2005, describes how faces can be identified from a video sequence and mentions a number of citations. The document "FRVT 2006 and ICE 2006 Large-Scale Results" by P. Jonathon Philips et al., Mar. 29, 2007, also deals with the identification of faces from digital image recordings and the algorithms used therein. This document in particular describes and evaluates the identification power of algorithms that are offered by various providers.

The aforementioned method for analyzing fingerprints or one of the algorithms on which the automatic recognition of faces is based can be implemented as image-processing software in the calculation unit 13. This can be used to determine precisely and evaluate differences in the reflection patterns occurring in the technologies described here.

Figure 6A:
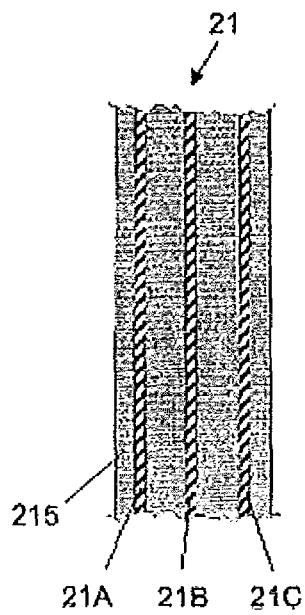
FIG. 6a shows a schematic illustration of a section of a carrier element.
Figure 6B:
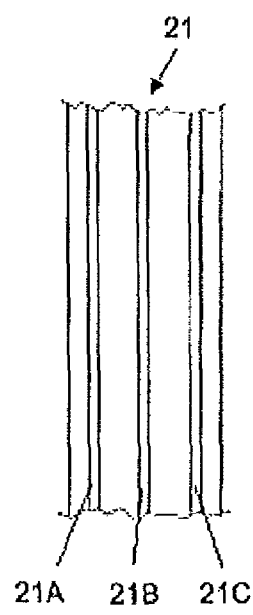
FIG. 6b shows an evaluation of the section from FIG. 6a by means of edge extraction in the case of an intact carrier element.
Figure 6C:
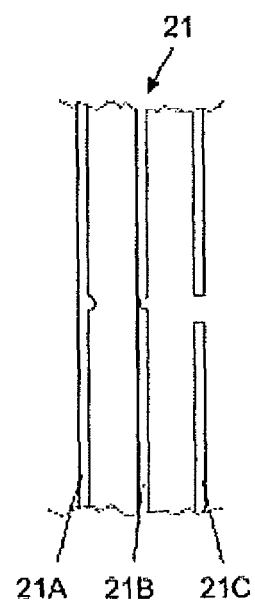
FIG. 6c shows an evaluation of the section from FIG. 6a by means of edge extraction in the case of a damaged carrier element.

In one exemplary embodiment, the image data are illustrated and evaluated in a coordinate system. Here, different evaluations of the image data are possible. By way of example, the profiles of the contours of the strands or wires are captured and analyzed. The wire contours typically have the same brightness profile over relatively long paths and it can be measured. Furthermore, the contours typically extend at least approximately in a straight line and in parallel. Intact contours therefore bring about straight and parallel contour profiles. If an anomaly, i.e. interruptions, bulges, etc., is now determined to occur within the extent of a contour, a corresponding error can be identified. As already mentioned previously, there are only blurred contours with a reduced image contrast if faults are present in and on the carrier element. An evaluation of such a contour profile is illustrated in exemplary and schematic fashion in FIGS. 6a to 6c. The transmission pattern and/or reflection pattern, recorded by the reception units (FIG. 6a), is resolved by means of edge extraction. In the case of an intact carrier element (FIG. 6b), this results in substantially straight lines which describe the peripheral edges of the individual ropes or strands (21A, 21B, 21C). A substantially intact, continuous line means that there is no substantial damage to the edge profile and hence to the carrier element. If the edge profile exhibits bulges (FIG. 6c, 21A), indentations (FIG. 6c, 21B) or interruptions (FIG. 6c, 21C), this indicates that the relevant rope or the strand is compressed, kinked or ripped in this region, or that a bundle of individual fibers of the rope or of the strand emerge from the rope or strand group. This can assess a state of the carrier element particularly well without needing to consult a reference image.

All possibly occurring defects are preferably classified and provided with associated feature data, which render it possible to search selectively for errors in the image data. This is how it is possible to analyze the image data quickly with a high hit probability.

As mentioned previously, interruptions, bulges or frays in contours of a reflection pattern can be associated with a fault in a wire 211 or strand. Areal, diffuse images can typically be identified as the formation of corrosion or wear debris.

The comparison of the transmission patterns and reflection patterns with a reference pattern which was generated for the relevant type of carrier elements is particularly advantageous. Further improvements can be obtained by virtue of reference patterns being newly formed after the installation of a carrier element 21 by virtue of the newly installed carrier element being run along and scanned. That is to say the "fingerprint" of a new carrier element 21 is recorded as the intended state thereof after it has been installed, and said fingerprint is stored in the storage unit 131 for future comparison measurements.

Comparison measurements according to the invention can be carried out with great precision within a short period of time. The carrier elements 21 can therefore be tested permanently and with minimal effort.

Here, provision can be made for various configurations of transmission units 11 and reception units 12D, 12R. In particular, a transmission unit 11 and a reception unit 12D or 12R can be integrated in a common module, which, for example, can be driven into any position by means of a controllable arm.

FIG. 2 shows a possible embodiment of the test device 1 with only one transmission unit 11 and two reception units 12D, 12R, which are installed on a rotatable or swivelable carrier ring 155 of an assembly device 15 by means of support element 151, 152, 153. The carrier ring 155, which is held and driven by means of a drive unit 150, can in this case be rotated or swiveled about the carrier element 21 such that the latter can be scanned from any side. The swivelable carrier ring is advantageous in that it does not need to enclose the carrier element 21 over the whole circumference. This allows a simple assembly of the carrier ring since it can be arranged on the carrier element at any point.

The transmission unit 11 and the first reception unit 12D are aligned against one another along the transmission axis sx which runs through the carrier element 21. The test radiation emitted along the transmission axis sx is reflected at the wire ropes 21A, 21B and is reflected at an acute angle a with a large radiation portion within a solid angle, the main axis of which forms the reflection axis rx. The angle a, which typically lies in the region of +/−60°, is preferably optimized on the basis of trials and can change depending on the configuration of the test device and of the carrier element 21.

FIG. 3 schematically shows a further exemplary embodiment of a test device 1 by means of which a flat carrier element 21 is tested, the latter having a sheath 215 in which, for example, four wire ropes 21A, 21B, 21C, 21D are integrated. The sheath 215, which has a rectangular cross section, protects the integrated wire ropes 21A, 21B, 21C, 21D from influences of the surroundings and therefore lengthens the service life thereof until the replacement state of wear. Here, the number of integrated wire ropes is selected depending on the load to be carried.

The carrier element 21 is arranged between a reception unit 120 and the transmission unit 11. Here, the carrier element 21 is arranged such that the transmission unit 11 emitting electromagnetic test radiation irradiates or illuminates a narrow side of the carrier element 21. As in the previous examples, the reception unit 120 is connected to the calculation unit 13.

In the arrangement of the carrier element 21 shown in FIG. 3, damage which occurs on one of the two wider sides of the carrier element 21 can predominantly be identified.

The described defects can also occur in a carrier element 21 of this type, as sketched out in FIG. 3. An interruption of a strand 211 has occurred in the integrated wire rope 21B and it subsequently penetrated the sheath 215 and is visible from the outside. Damage to the sheath 215 has occurred at the same time. By means of an optical test of the carrier element 21 by means of the reception unit 120 it is possible to identify this error. In one embodiment, the reception unit 120 is a digital camera, which stores individual digital images or a sequence of digital images with a predetermined resolution.

The reception unit 120 therefore captures electromagnetic radiation, in the visible wavelength region, which is reflected at the carrier element 21. This electromagnetic radiation can be daylight in one exemplary embodiment if it is sufficiently bright in the elevator shaft 6. If this is not the case, an arbitrary light source, for example illumination provided in the elevator shaft 6, can serve all transmission unit 11. However, provision is preferably made for a separate light source 11 which illuminates the scanned part of the carrier element 21 in optimum fashion. Hence the reception unit 120 captures directly incident transmission radiation 8T and reflection radiation 8R, reflected on the surface of the carrier element 21, and supplies corresponding image data to the calculation unit 13. By evaluating the image data it is possible automatically to identify visually identifiable defects, such as broken open and outwardly emerging wires 211 and damage 2151 to the sheath 215, as illustrated on the screen of the calculation unit 13.

FIG. 4 schematically shows a further exemplary embodiment of a test device 1, by means of which a flat carrier element 21 is tested. Here, the carrier element 21 is arranged in front of a reception unit 120, to be precise such that a wide side of the carrier element 21 lies opposite the reception unit 120. The previously shown connection to the calculation unit 13 has not been shown in FIG. 4 for reasons of clarity.

Light—daylight or artificial light—is reflected on the surface of the wide side of the carrier element 21 and impinges on the reception unit 120. The reception unit 120, which can as described previously be a digital camera, records individual digital images or a sequence of digital images and stores these.

In the arrangement of the carrier element 21 shown in FIG. 4, it is predominantly damage which occurs on the wide side of the carrier element 21 facing the reception unit 120 that can be identified.

If the at least one reception unit 12D, 12R, 120 is arranged at a relatively large distance from the carrier element 21 and subjected to movements, e.g. vibrations, this results in greater effort for image capture and image processing. FIG. 5 shows a test device 1 that can be coupled to the carrier element 21 and that can be used to avoid these disadvantages.

The exemplary embodiment of the test device 1 shown in FIG. 5 has a housing 100 with two housing parts 100A, 100B, which are interconnected by holders 102. Arranged in the first housing part 100A there is the transmission unit 11 and a first reception unit 12R, which serves for imaging reflection patterns. A second reception unit 12D is provided in the second housing part 100B and it serves for imaging transmission patterns. In this example, the holders 102 simultaneously serve as bearing shafts for optional running wheels 101, which can roll down the narrow side surfaces on both sides of the carrier element 21. In one exemplary embodiment, which is shown in FIG. 5, the running wheels 101 can roll down along sliding surfaces 2150 present on the carrier element 21.

Naturally, the housing 100A, 100B can also be embodied such that running wheels or guide surfaces guide the carrier element 21 at the longitudinal sides thereof. Particularly if grooved surfaces of the carrier element are used, for example in the case of a V-ribbed belt, guidance by means of this grooved surface is expedient.

In another exemplary embodiment of the test device 1, the housing 100 only has a single reception unit. Here, the reception unit is dimensioned and arranged such that it can record an image of the whole width of the carrier element 21. The reception unit can therefore contain a single, appropriately dimensioned sensor element (sensor array) or a plurality of individual sensor elements arranged next to one another, which are then connected appropriately. The reception unit is arranged on the same side as the transmission unit 11, which illuminates the wide side of the carrier element 21. Reflected light is then recorded by the reception unit, analogously to as in FIG. 4.

The shown test device 1 therefore can be displaced along the carrier element 21 or be kept stationary while the carrier element 21 moves. In any case, the at least one transmission unit 11 and the reception units 12D and 12R are kept at a constant distance from the carrier element 21. This is how it is possible to make high-quality image recordings and evaluate these with minimal effort.

Test devices 1 according to the invention in the various embodiments are preferably installed in the vicinity of the drive pulley 24 and hence in a region through which the elevator car 22 does not pass and which, at the same time, allows an analysis of almost a whole length of the carrier element.

In accordance with the provisions of the patent statutes, the present invention has been described in what is considered to represent its preferred embodiment. However, it should be noted that the invention can be practiced otherwise than as specifically illustrated and described without departing from its spirit or scope.

The invention claimed is:

1. A method for testing at least one carrier element of an elevator installation in which the carrier element carries an elevator car, wherein the carrier element is a sheathed carrier element, comprising the following steps:

activating a transmission unit 'for emitting electromagnetic' radiation directed at the carrier element;

activating a reception unit for receiving the electromagnetic radiation to generate test data representing a current state of the carrier element from the received electromagnetic radiation;

evaluating the test data in a calculation unit to determine a deviation of the test data from reference data representing an intended state of the carrier element, wherein the reception unit is responsive to electromagnetic radiation with a wavelength in a range of between 90 µm and 120 µm;

generating from the calculation unit an output signal representing the determined deviation to at least one of present a visual display and control a drive unit driving the carrier element of the elevator installation; and including at least one of:

rotating or swiveling the transmission unit about the carrier element between at least two positions to scan the carrier element from at least two sides;

rotating or swiveling the at least one reception unit about the carrier element between at least two positions to scan the carrier element from at least two sides; and arranging at least two of the reception units around the carrier element to scan the carrier element from different sides.

2. The method according to claim 1 wherein the test data includes a first digital image, the reference data representing the intended state of the carrier element includes a stored second digital image and the evaluating is a comparison of the first and second digital images.

3. The method according to claim 1 wherein the test data represents at least one of transmission patterns and reflection patterns and the reference data represents reference patterns for determining deviations from the intended state of the carrier element.

4. A method for testing at least one carrier element of an elevator installation in which the carrier element carries an elevator car, wherein the carrier element is a sheathed carrier element, comprising the following steps:
   activating a transmission unit for emitting electromagnetic radiation directed at the carrier element;
   activating a reception unit for receiving the electromagnetic radiation to generate test data representing a current state of the carrier element from the received electromagnetic radiation;
   evaluating the test data in a calculation unit to determine a deviation of the test data from reference data representing an intended state of the carrier element, wherein the reception unit is responsive to electromagnetic radiation with a wavelength in a range of between 90 µm and 120 µm;
   generating from the calculation unit an output signal representing the determined deviation to at least one of present a visual display and control a drive unit driving the carrier element of the elevator installation, wherein the reception unit receives the electromagnetic radiation as test radiation that at least one of extends parallel to a transmission axis passing through the carrier element and, starting from the carrier element, is reflected along at least one reflection axis, and wherein the test data are transmission patterns and reflection patterns respectively, the calculation unit evaluating the patterns to detect surface changes on the carrier element; and
   including at least one of:
      monitoring a diameter of the carrier element to establish a reduction or widening of the carrier element representing internal errors of wires, strands or fibers of the carrier element; and
      generating reflection patterns of the carrier element for the electromagnetic radiation transmitted along the reflection axis to establish axial stretches in the reflection pattern representing internal errors of wires, strands or fibers of the carrier element.

5. The method according to claim 4 wherein the transmission unit emits the electromagnetic radiation with a wavelength in the range of between 90 µm and 120 µm along the transmission axis.

6. The method according to claim 4 wherein an angle between the at least one reflection axis and the transmission axis extends along an arc from the transmission unit to the reception unit and lies in a range of between 0° and 90° or in a range of between 0° and −90°.

7. The method according to claim 4 wherein an angle between the at least one reflection axis and the transmission axis extends along an arc from the transmission unit to the reception unit and lies in a range of between 0° and 60° or in a range of between 0° and −60°.

8. The method according to claim 4 including the steps of:
   imaging the test data in two dimensions; and
   at least one of determining faults for the electromagnetic radiation transmitted along the transmission axis to establish interruptions or indentations in wires or fibers of the carrier element, and determining faults for the electromagnetic radiation transmitted along the reflection axis to establish interruptions or indentations in wires or fibers of the carrier element.

9. A device for testing a carrier element of an elevator installation in which the carrier element carries an elevator car, wherein the carrier element includes a sheath, comprising:
   a transmission unit for emitting electromagnetic test radiation directed at the carrier element;
   a reception unit for receiving the electromagnetic test radiation directed at the carrier element, wherein the reception unit generates test data representing the received electromagnetic test radiation with a wavelength in a range of between 90 µm and 120 µm;
   a calculation unit coupled to the reception unit for evaluating the test data to determine a deviation of the test data from reference data representing an intended state of the carrier element and for generating an output signal representing the determined deviation to at least one of a visual display and a control unit driving the carrier element; and
   including at least one of:
      an assembly device for rotating or swiveling the transmission unit about the carrier element between at least two positions to scan the carrier element from at least two sides;
      an assembly device for rotating or swiveling the at least one reception unit about the carrier element between at least two positions to scan the carrier element from at least two sides; and
      at least two of the reception units arranged around the carrier element to scan the carrier element from different sides.

10. The device according to claim 9 wherein the reception unit generates the test data as a first digital image and the calculation unit compares the first digital image to a stored second digital image representing the intended state of the carrier element.

11. The device according to claim 10 wherein the reception unit receives the test radiation as at least one of test radiation that extends parallel to a transmission axis passing through the carrier element and, starting from the carrier element, test radiation that is reflected along a reflection axis, and wherein the test data generated by the reception unit is imaged in the calculation unit as transmission patterns and reflection patterns respectively, and evaluated by the calculation unit to establish surface changes on the carrier element.

12. The device according to claim 11 wherein the reception unit is aligned along the transmission axis and a second reception unit is aligned along the reflection axis, wherein an angle that is included by the reflection axis and the transmission axis extends in an arc from the transmission unit to the second reception unit and lies in a range of between 0° and 90° or in a range of between 0° and −90°.

13. The device according to claim 11 wherein the reception unit is aligned along the transmission axis and a second reception unit is aligned along the reflection axis, wherein an angle that is included by the reflection axis and the transmission axis extends in an arc from the transmission unit to the second reception unit and lies in a range of between 0° and 60° or in a range of between 0° and −60°.

14. The device according to claim 9 wherein the calculation unit is connected to a database in which reference patterns are stored as the reference data.

15. The device according to claim 9 wherein the transmission unit and the reception unit are integrated into a module adapted to be coupled to the carrier element.

* * * * *